US00PP32152P2

(12) United States Plant Patent
Hanes

(10) Patent No.: US PP32,152 P2
(45) Date of Patent: Sep. 1, 2020

(54) ***CALIBRACHOA* PLANT NAMED 'CBRZ0029'**

(50) Latin Name: *Calibrachoa hybrida*
Varietal Denomination: CBRZ0029

(71) Applicant: SYNGENTA CROP PROTECTION AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,621

(22) Filed: May 15, 2019

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/025; A01H 5/12; A01H 6/82; A01H 6/00; A01H 5/00; A01H 6/821; A01H 6/14
See application file for complete search history.

*Primary Examiner* — June Hwu
(74) *Attorney, Agent, or Firm* — Dale Skalla

(57) ABSTRACT

A new *Calibrachoa* plant named 'CBRZ0029' particularly distinguished cultivar has mid-sized raspberry colored flowers with a darker "eye" and yellow inside the flower at the base of the petals, green foliage, good branching, semi-trailing plant habit, and has little sensitivity to soil pH.

1 Drawing Sheet

Latin name of the genus and species of the plant claimed: *Calibrachoa hybrida.*

Varietal denomination: 'CBRZ0029'.

BACKGROUND OF THE NEW PLANT

The present invention comprises a new *Calibrachoa*, botanically known as *Calibrachoa hybrida*, and hereinafter referred to by the variety name 'CBRZ0029'.

'CBRZ0029' is a product of a planned breeding program. The new cultivar has mid-sized raspberry colored flowers with a darker "eye" and yellow inside the flower at the base of the petals, green foliage, good branching, semi-trailing plant habit, and has little sensitivity to soil pH.

'CBRZ0029' originated from a hybridization made in October 2014 in a greenhouse in Gilroy, Calif., USA. The female parent was an unpatented proprietary breeding line known as '4135-1', which had flowers that were light raspberry with a darker center and the plant had compact growth. It originated from a seedling selected in Gilroy, Calif. The male parent of 'CBRZ0029' was an unpatented proprietary plant with raspberry with a darker center flowered plant, known as '4132-3', originating from a seedling selected in Gilroy, Calif. The male parent differs from 'CBRZ0029' in that it is more upright, has fewer flowers, and is later to flower.

The resulting seeds were sown in February 2015 and 'CBRZ0029' was selected as one flowering plant within the progeny of the stated cross in May 2015 in a controlled environment in Gilroy, Calif.

The first act of asexual reproduction of 'CBRZ0029' was accomplished when vegetative stem cuttings were propagated from the initial selection in the summer of 2015 in a controlled environment in Gilroy, Calif.

BRIEF SUMMARY OF INVENTION

Horticultural examination of plants grown from cuttings of the plant initiated in the spring of 2016, and continuing thereafter, has demonstrated that the combination of characteristics as herein disclosed for 'CBRZ0029' are firmly fixed and are retained through successive generations of asexual reproduction.

'CBRZ0029' has not been observed under all possible environmental conditions. The phenotype may vary significantly with variations in environment such as temperature, light intensity, and day length.

A Plant Breeder's Right for this cultivar has not yet been applied for. 'CBRZ0029' has not been made publicly available prior to the effective filing date of this application, notwithstanding any disclosure that may have been made less than one year prior to the effective filing date of this application by the inventor or another who obtained 'CBRZ0029' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

Figure 1:
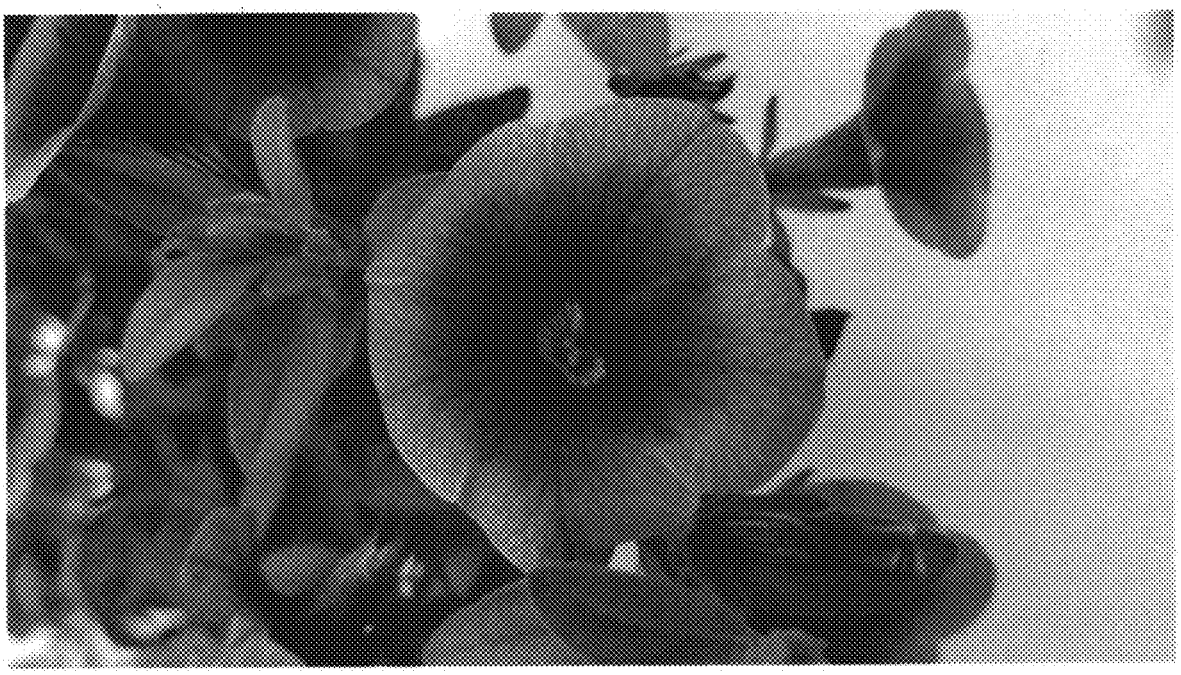
Figure 2:
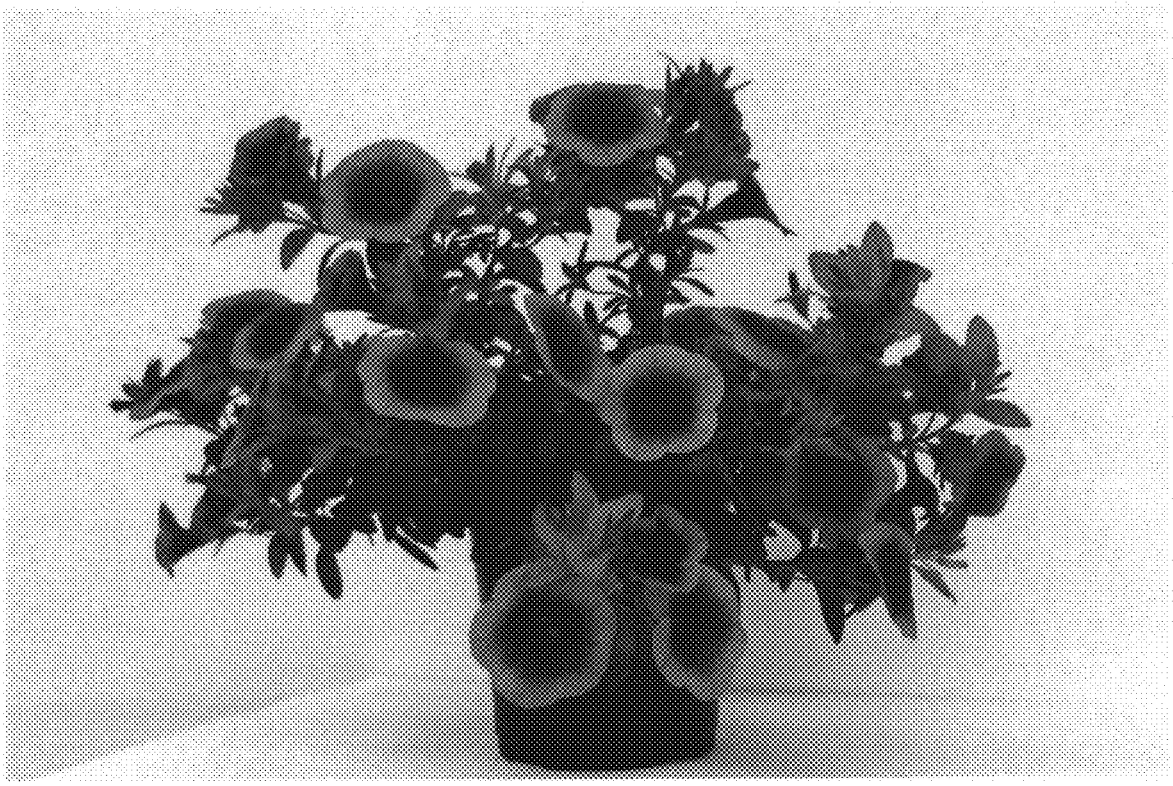

The accompanying photographic drawings show typical flower and foliage characteristics of 'CBRZ0029' with colors being as true as possible with an illustration of this type. The photographic drawings show in FIG. 1. a close-up of the flowers and in FIG. 2. a flowering plant of the new variety.

DETAILED BOTANICAL DESCRIPTION

The aforementioned photographs were taken in the greenhouse in Gilroy, Calif. in February 2019.

The measurements and observations were made in February 2019 in Gilroy, Calif. on plants grown in 4 inch pots in the greenhouse.

Color references are made to The Royal Horticultural Society Colour Chart (R.H.S.) 2015.

TABLE 1

DIFFERENCES BETWEEN THE NEW VARIETY 'CBRZ0029' AND A MOST SIMILAR VARIETY

| | 'CBRZ0029' | 'Cabrio Pink with Eye' (Not patented) |
|---|---|---|
| Main flower color: | Raspberry colored flowers with a darker "eye" and yellow inside the flower at the base of the petals | Pink with blue tone, darker pink center with radiating yellow |
| Veins in flower, upper corolla surface: | Present and noticeable | Absent or very faint |
| Plant habit as a young plant: | More trailing | More round |

Plant:

*Form, growth and habit.*—Semi-upright and spreading stems, with good branching.

*Plant height.*—10-12 cm.

*Plant height (inflorescence included).*—13-14 cm.

*Plant width.*—30-38 cm.

*Quantity of main branches.*—8-9.

*Quantity of secondary branches.*—2-4 per basal branch.

*Time to produce a flowering plant.*—7-8 weeks for a 12 cm pot (from planting of rooted cuttings).

Roots:

*Number of days to initiate.*—18-21 days at about 22° C.

*Number of days to produce a rooted cutting.*—21-24 days at 22° C.

*Type.*—Fibrous.

*Color.*—RHS 158D.

Stem:

*Color of stem.*—Mainly RHS 145A.

*Length of stem.*—Approximately 18-20 cm.

*Diameter.*—0.15-0.2 cm.

*Length of internodes.*—1.7-2.0 cm.

*Texture.*—Short hairs along the stem.

Foliage:

*Immature leaf, color of upper surface.*—RHS 146A.

*Immature leaf, color of lower surface.*—RHS 146C.

*Mature leaf, color of upper surface.*—RHS 146A.

*Mature leaf, color of lower surface.*—RHS 146B.

*Leaf blade, length.*—2.8-3.0 cm.

*Leaf, width.*—0.7-0.8 cm.

*Shape.*—Elliptical, narrow.

*Base shape.*—Acuminate.

*Apex shape.*—Obtuse.

*Margin.*—Entire.

*Texture, upper and lower surfaces.*—Micro hairs.

*Color of veins, upper surface.*—RHS 146A.

*Color of veins lower surface.*—RHS 146C.

*Petiole color.*—RHS 146B.

*Petiole length.*—0.1-0.3 cm.

*Diameter of petiole.*—0.1-0.2 cm.

*Texture.*—Hairy.

Inflorescence:

*Type.*—Flowers solitary in upper leaf axis and slanting upright or outwards.

*Quantity of inflorescences per plant.*—Approximately 45-47 flowers.

*Lastingness of individual flowers.*—About 7-9 days.

*Fragrance.*—None.

*Duration of flowering.*—Continuous flowering throughout the summer.

Pedicel:

*Color of pedicel.*—RHS 146D.

*Length of pedicel.*—0.3-0.5 cm.

*Diameter of pedicel.*—0.1 cm.

*Texture of pedicel.*—Micro hairs.

Flower:

*Immature flowers, corolla upper surface.*—RHS 71A with a margin of RHS 71C.

*Immature flowers, corolla lower surface.*—RHS 153C but with a RHS 83A net like veination going down the lower surface.

*Mature flowers, color upper surface.*—Outer ring with medium amount RHS 70B with inner ring with a glossy look between RHS N79B and RHS N79C.

*Mature flowers, color lower surface.*—Corolla tube is RHS 71A and is RHS 71C and 71D on the petal margin.

*Mature flower vein conspicuousness of the upper surface.*—Medium.

*Flower horizontal diameter.*—3.9-4.0 cm.

*Flower height (vertical).*—1.4-1.6 cm.

*Corolla tube length.*—1.1 cm.

*Petal apex shape.*—Truncate.

*Margin.*—Entire.

*Waviness of petals.*—Weak to medium.

*Petal lobation.*—Moderate.

*Corolla texture.*—'Face' papillose and glabrous; rear side with short hair.

*Corolla tube.*—RHS 151D at base and RHS 61A at upper region of the throat.

*Conspicuousness of the inner corolla tube veins.*—Strong.

Bud (just before opening):

*Color at apex.*—RHS N79C.

*Length.*—2.8-3.0 cm.

*Width (upper end).*—0.5-0.6 cm.

*Shape.*—Oblong.

Calyx:

*Number of sepals.*—5.

*Color of sepals, adaxial or upper surface.*—RHS 138A.

*Color of sepals, abaxial or lower surface.*—RHS 138A.

*Length of sepals.*—10-11 mm.

*Width of sepals.*—0.5 cm.

*Sepal shape.*—Lanceolate.

*Apex shape.*—Obtuse to acute.

*Margins.*—Entire.

*Texture.*—Hairless sepals.

Reproductive organs:

*Pistil.*—1.

*Length.*—1.2-1.3 cm.

*Style color.*—RHS 144B.

*Style length.*—0.8-0.9 cm.

*Stigma color.*—RHS 144B.

*Number of stamens.*—5.

*Color of filaments.*—RHS 4D.

*Length filaments.*—1.1-1.2 cm.

*Color of pollen.*—RHS 13B.

*Pollen amount.*—Moderate.

*Fertility/seed set.*—Not observed on this hybrid.

*Disease/pest resistance.*—Not observed on this hybrid.

What is claimed is:

1. A new and distinct variety of *Calibrachoa* plant named 'CBRZ0029', substantially as illustrated and described herein.

* * * * *